United States Patent [19]

Bellasio et al.

[11] 4,016,162
[45] Apr. 5, 1977

[54] 6-MORPHOLINO-3-SUBSTITUTED PHENYL-S-TRIAZOLO[4,3-b]PYRIDAZINES

[75] Inventors: Elvio Bellasio, Como; Ambrogio Campi, Milan, both of Italy

[73] Assignee: Gruppo Lepetit S.p.A., Milan, Italy

[22] Filed: Apr. 8, 1976

[21] Appl. No.: 674,790

Related U.S. Application Data

[63] Continuation of Ser. No. 522,412, Nov. 11, 1974, abandoned.

[30] Foreign Application Priority Data

Aug. 27, 1974 South Africa .................... 74/5482

[52] U.S. Cl. .................. 260/247.5 DP; 424/248.4; 424/248.58
[51] Int. Cl.² ....................................... C07D 487/04
[58] Field of Search ........................... 260/247.5 DP

[56] References Cited

FOREIGN PATENTS OR APPLICATIONS 1,248,409   11/1960   France ............................ 260/247.5

OTHER PUBLICATIONS

Yurugi et al., "Chem. Abstracts," vol. 80, (1974), No. 37073d.

*Primary Examiner*—Henry R. Jiles
*Assistant Examiner*—R. W. Ramsuer
*Attorney, Agent, or Firm*—Maynard R. Johnson

[57] ABSTRACT

6-Morpholino-3-substituted phenyl triazolopyridazine compounds such as 8-methyl-6-morpholino-3-phenyl-s-triazolo[4,3-b]pyridazine or 8-methyl-6-morpholino-3-(3,4,5-trimethoxyphenyl)-s-triazolo[4,3-b]pyridazine are prepared by the reaction of the corresponding substituted benzoyl halide with a 3-hydrazino-6-morpholinopyridazine in the presence of a hydrogen chloride acceptor or by the reaction of a 3-halo-6-morpholinopyridazine with a corresponding substituted benzoyl hydrazide. The compounds have pharmacological activity as bronchodilators.

7 Claims, No Drawings

6-MORPHOLINO-3-SUBSTITUTED PHENYL-S-TRIAZOLO[4,3-b]PYRIDAZINES

This is a continuation of application Ser. No. 522,412, filed Nov. 11, 1974, now abandoned.

BACKGROUND OF THE INVENTION

The compounds of the invention can be prepared by methods analogous to those described by Pollak et al., Tetrahedron 22, 2073 (1966). Other methods are described in Miller and Rose, J. Chem, Soc. 1963, 5642: Basu and Rose, J. Chem. Soc. 1963, 5660 (1963); and Davies et al., Nature, 234 50 (1971).

The compound 3-morpholino-6-methyl-8-phenyl-s-triazolo[4,3-b]pyridazine was described by Yurugi et al., Takeda Kenkyusho 32 (2), 111–117 (1973). Other morpholino triazolopyridazines are described in French Pat. No. 1248409 and in Chemical Abstracts, 67 21884q.

SUMMARY OF THE INVENTION

The present invention relates to new pharmacologically active heterocyclic compounds. More particularly, the invention relates to 6-morpholino-3-substituted phenyl-s-triazolo[4,3-b]pyridazines corresponding to the formula

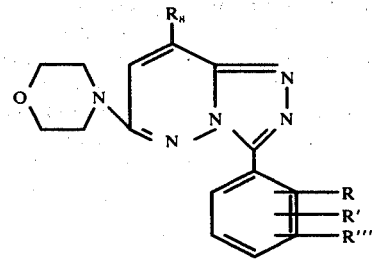

wherein R, R' and R'' each independently represent hydrogen, hydroxy, loweralkyl, lower alkoxy, halo and nitro, and wherein $R_8$ represents hydrogen or loweralkyl; and to pharmacologically acceptable salts of said compounds. In the present specification and claims the terms loweralkyl and lower alkoxy refer to loweralkyl or lower alkoxy of one, two or three carbon atoms; and halo refers to fluoro, chloro or bromo. It is understood that the invention is inclusive of subgroups of compounds of the above formula, for example, those wherein R is hydrogen; those wherein R, $R_8$ and R' are hydrogen; those wherein R, R' and R'', represent hydrogen or the same loweralkyl, lower alkoxy, halo or nitro or the same loweralkyl, lower alkoxy, halo or nitro substituent; those wherein R, R' and R'' are halo or nitro; those wherein R, R', and R'' are other than halo; etc. Such subgroups are apparent from the above description and the following specification; and further listing is omitted for the sake of brevity. Preferred groups of compounds comprise those wherein the loweralkyl and lower alkoxy groups are of one carbon atom; those wherein $R_8$ is hydrogen; those wherein the halo substituent is chloro; those wherein the loweralkyl and lower alkoxy substituents are of one carbon atom and the halo substituent is chloro; those wherein R, R' and R'' are other than hydroxy, and a particularly preferred compound is the compound wherein R, R', R'', and $R_8$ (the 8-position substituent) are all hydrogen.

The 6-morpholino-3-substituted phenyl-s-triazolo[4,3-b]pyridazine compounds corresponding to the above formula and their pharmacologically acceptable salts have useful biological activity as bronchodilators and also have a desirably low toxicity.

As employed herein, the phrase pharmacologically acceptable salt refers to salts of the morpholino substituted-phenyl triazolopyridazines, the anions of which are relatively nontoxic and innocuous to mammals at dosages consistent with good biological activity so that side effects ascribable to the anions do not vitiate the beneficial effects of the triazolopyridazine compounds. Suitable pharmacologically acceptable salts can be prepared by conventional procedures such as dissolving the free base compound in an inert organic solvent such as ether and treating the resulting solution with an excess ether solution of a suitable pharmacologically acceptable acid such as hydrochloric acid.

For the sake of brevity, such compounds will be hereinafter referred to simply as "triazolopyridazines."

The compounds of the invention are prepared by the reaction of a 3-substituted-6-morpholinopyridazine of formula II with a substituted benzoyl compound of formula III

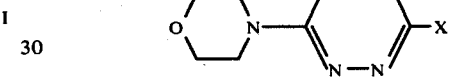

wherein $R_8$, R, R' and R'' have the above significance and wherein X and Y are selected from halo and a hydrazine residue-$NH-NH_2$, X and Y being different and one of them being a hydrazine residue.

Thus, the compounds of the invention can be prepared by reacting a 3-hydrazino-6-morpholinopyridazine of formula II wherein X is hydrazine residue with a substituted benzoyl halide of formula III wherein Y is halo. This reaction proceeds when the reactants are contacted and mixed, preferably at boiling temperature of the reaction mixture under reflux. The reaction is preferably carried out in an inert organic liquid, such as dioxane as a reaction medium and in the presence of an organic base as a hydrogen halide acceptor. The proportions of the reactants can be varied considerably. However, the reaction consumes the reactants and the hydrogen halide acceptor in equimolar proportions, and the use of the materials in approximately such proportions is convenient. The product can be recovered from the reaction mixture by evaporation to remove the reaction medium and can be purified by conventional procedures such as recrystallization and washing.

The compounds can also be prepared by the reaction of a 3-halo-6-morpholinopyridazine of formula II wherein X is halo with a benzoyl hydrazide of formula III wherein Y is a hydrazine residue. The reaction of the 3-halo-6-morpholinopyridazine and the benzoyl hydrazide proceeds when the reactants are contacted and mixed at an elevated temperature, preferably from about 150°–200° C. The reaction can be carried out in the presence of an inert organic solvent which has a boiling temperature within or above the reaction temperature range, and can be conveniently carried out in the absence of the solvent. The proportions of the reactants can be varied considerably, however, the reactants are consumed in equimolar proportions, and are conveniently employed in approximately such proportions. The reaction proceeds rapidly, in most cases with the evolution of heat of reaction and hydrogen chloride of reaction. In most cases a significant yield of the product is obtained after from about 15 minutes to about 45 minutes. The product can be separated from the reaction mixture by evaporation of the inert organic solvent, when a solvent is used. The product can also be separated by conventional procedures such as partitioning between an organic solvent and an aqueous base, followed by evaporation of the organic solvent and purification by conventional procedures such as recrystallization and washing.

In a convenient procedure, approximately equimolar proportions of the 3-halo-6-morpholinopyridazine and benzoyl hydrazide reactants are mixed together under a nitrogen blanket and the mixture is heated to a temperature of from about 150° to about 200° C. When the reactants have melted, the mixture is stirred, and generally within a short period of time (about 5 to 15 minutes), the reaction mixture gives off heat and hydrogen halide of reaction. After a brief reaction period, generally from about 15 to 30 minutes, the reaction mixture is cooled and partitioned between an organic solvent such as chloroform, methylene chloride or the like and an aqueous base such as aqueous sodium carbonate or sodium hydroxide. The organic phase is separated, dried and evaporated in vacuo; and the product is recovered from the residue and purified by conventional procedures such as recrystallization and washing.

The second above-described procedure, the reaction of a 3-halo-6-morpholinopyridazine with a benzoyl hydrazide is a preferred method of carrying out the general synthesis of the triazolopyridazine compounds of the invention. Either method of carrying out the general synthesis can be employed, however, and the appropriate starting materials for either method of carrying out the general synthesis can be prepared by procedures which are known.

The following examples illustrate the invention.

EXAMPLE 1

1.48 Grams of 3-hydrazino-4-methyl-6-morpholinopyridazine and 1.8 grams of triethylamine are dissolved in 200 milliliters of dioxane. 3.5 Grams benzoyl chloride are added to the resulting mixture, and the mixture is heated at the boiling temperature under reflux for 3 hours. The mixture is evaporated to dryness, and the 8-methyl-6- -morpholino-3-phenyl-s-triazolo[4,3-b]pyridazine product is obtained as a residue. The product is washed with water, recrystallized from ethanol and found to melt at a temperature of 271°–273° C. 3.6 Grams of the product are obtained.

EXAMPLE 2

39 Grams of 3-hydrazino-6-morpholinopyridazine is added portionwise to 30 grams of benzoyl chloride. The mixture is heated at a temperature of 130°–140° C. for 1 hour. The mixture is then cooled and the residue of the reaction mixture is neutralized by the addition of aqueous sodium bicarbonate solution. The resulting aqueous mixture is then extracted with chloroform. The chloroform extract is washed with water, dried over anhydrous sodium sulfate and evaporated to dryness under reduced pressure. The 6-morpholino-3-phenyl-s-triazolo[4,3-b]pyridazine product is obtained as a residue from the evaporation. The product is crystallized twice from isopropanol and found to melt at 195°–196° C. 15 Grams of the named product are obtained. The structure of the product is confirmed by infrared spectroscopy and by nuclear magnetic resonance analysis.

EXAMPLE 3

3-Chloro-4-methyl-6-morpholinopyridazine (21.4 grams; 0.1 mol) and 15.0 grams (0.1 mol) of 4-methylbenzoyl hydrazide are mixed together and stirred at a temperature of 155° C. using an oil bath. The mixture is observed to melt, and after about 10 minutes following completion of melting a vigorous reaction is observed in the reaction vessel. The reaction vessel is maintained in the heated oil bath for an additional 5 minutes, and then cooled to room temperature. The reaction mixture is partitioned between methylene chloride and saturated aqueous sodium bicarbonate solution and the methylene chloride layer is filtered, washed with water, dried over anhydrous sodium sulfate and filtered again. The methylene chloride solution is then evaporated to dryness under reduced pressure, and 13.95 grams of the 6-morpholino-3-(4-tolyl)-8-methyl-s-triazolo[4,3-b]pyridazine product are obtained. The product is taken up in boiling isopropanol, filtered, crystallized from the filtrate on cooling and separated by filtration. The product is found to melt at a temperature of 295°–296° C. Structure of the product is confirmed by infrared spectroscopy and by elemental analysis.

EXAMPLE 4

3-Chloro-6-morpholinopyridazine (19.97 grams; 0.1 mol) and 3-nitrobenzoyl hydrazide (18.11 grams; 0.1 mol) are mixed together in a reaction vessel preheated to 185° C. in an oil bath. The mixture is stirred under a nitrogen blanket while heating in the oil bath is continued for 30 minutes. The reaction mixture is then cooled to room temperature and partitioned between methylene chloride and saturated aqueous sodium bicarbonate solution. The mixture is filtered, the methylene chloride layer is separated; and the methylene chloride layer is then washed with water, dried with anhydrous sodium sulfate, filtered and evaporated to dryness. The 6-morpholino-3-(3-nitrophenyl)-s-triazolo[3,2-b]pyridazine product is crystallized from isopropanol and obtained as a yellow solid which is observed to fuse at about 199° C. and to melt in the temperature range 237°–249° C. (23.8 percent yield).

6-Morpholino-8-methyl-3-(3-nitrophenyl)-s-triazolo[4,3-b]pyridazine is similarly prepared and found to melt at 245°–247° C., (yield 40 percent).

EXAMPLE 5

3-Chloro-4-methyl-6-morpholinopyridazine (21.36 grams; 0.1 mol) and 18.1 grams (0.1 mol) of 2-nitrobenzoyl hydrazide are mixed together in a reaction vessel which has been preheated to 185° C. in an oil bath. Heating is continued at 185° C. for 30 minutes during which time a vigorous reaction is observed, beginning about 7 minutes after completion of melting of the reactants. The flask is cooled to room temperature and the reaction mixture is partitioned between methylene chloride and saturated aqueous sodium bicarbonate solution. The mixture is filtered; the methylene chloride layer is separated and washed with water, and the methylene chloride is dried with anhydrous sodium sulfate and evaporated under reduced pressure. The residue is taken up in 500 milliliters of boiling isopropanol and filtered. The 6-morpholino-3-(2-nitrophenyl)-8-methyl-s-triazolo[3,2-b]pyridazine product is obtained as a filter cake. The product is found to melt at 198°–200° C.; as 20.4 grams of the product are obtained. This represents a 59.9 percent yield based on the amount of the starting material employed. The product is found by elemental analysis to have carbon, hydrogen, and nitrogen contents of 56.3, 5.0, 24.4 percent, respectively, as compared with the theoretical contents of 56.5, 4.7, and 24.7 percent, respectively, calculated for the named structure.

EXAMPLE 6

3-Chloro-6-morpholinopyridazine (18.6 grams; 0.9 mol) and 4-chlorobenzoyl hydrazide (15.9 grams; 0.9 mol) are mixed together in a glass reaction vessel which has been preheated in an oil bath to a temperature of 110° C. The reactants are mixed under a nitrogen blanket and mixing is continued as the temperature is increased slowly to 190°–195° C. The reactants are observed to melt and a vigorous reaction is observed to start about 3 minutes after melting. Heating at 190°–195° C. is continued for 25 minutes, after which the reaction mixture is cooled to room temperature and partitioned between methylene chloride and aqueous saturated sodium bicarbonate solution. The methylene chloride layer is washed with water, dried over anhydrous sodium sulfate and evaporated to dryness. The 6-morpholino-3-(4-chlorophenyl)-s-triazolo[4,3-b]pyridazine product obtained as the residue is recrystallized from ethanol and found to melt at 235°–237° C. The product is found by elemental analysis to have carbon, hydrogen and nitrogen contents of 57.27, 4.57 and 22.03 percent, respectively as compared to the contents of 57.05, 4.47, and 22.18 percent, respectively, calculated for the named structure.

EXAMPLE 7

3-Chloro-6-morpholinopyridazine (19.96 grams; 0.1 mol) and 3,4-dichloro benzoylhydrazide (20.5 grams; 0.1 mol) are mixed together and heated under a nitrogen blanket at a temperature of 170° C. After the reactants are observed to melt, heating is continued for 20 minutes at 170° C, after which the reaction mixture is cooled to room temperature. The mixture is partitioned between methylene chloride and saturated aqueous sodium bicarbonates solution and the mixture is filtered. The methylene chloride layer is separated, washed once with water, dried over anhydrous sodium sulfate, filtered and evaporated to dryness. 17.5 grams of the 6-morpholino-3-(3,4-dichlorophenyl)-s-triazolo[4,3-b]pyridazine product are obtained. The product is crystallized from boiling ethanol and the crystallized product is found to melt at a temperature of 264°–265° C. The structure of the product is confirmed by elemental analysis.

EXAMPLE 8

Benzoylhydrazide (13.6 gram; 0.1 mol) and 3-chloro-6-morpholinopyridazine (19.96 grams; 0.1 mol) are heated under a nitrogen blanket with stirring for 20 minutes at 150° C. The reaction mixture is cooled, partitioned between saturated aqueous sodium bicarbonate solution and methylene chloride, and the methylene chloride extract dried over anhydrous sodium sulfate and evaporated under reduced pressure. The product is redissolved in methylene chloride and ether is added to the solution until the product precipitates. The precipitate is then recrystallized from isopropanol to obtain 8 grams (28.4 percent yield) of 6-morpholino-3-phenyl-s-triazolo[4,3-b]pyridazine, the compound of Example 2. Structure of the product is confirmed by infrared spectroscopy.

In similar procedures, the following are prepared:

8-Methyl-6-morpholino-3-(4-methoxyphenyl)-s-triazolo[4,3-b]pyridazine, melting at 266°–268° C.;

6-Morpholino-3-(4-chloro-2-methylphenyl)-s-triazolo[4,3-b]pyridazine, molecular weight 330;

6-Morpholino-3-(3-methoxy-4-methylphenyl)-s-triazolo[4,3-b]pyridazine, melting at 215°–220°;

6-Morpholino-3-(4-methoxyphenyl)-s-triazolo[4,3-b]pyridazine, melting at 244°–247° C,;

6-Morpholino-8-propyl-3-(4-methylphenyl)-s-triazolo[4,3-b]pyridazine, molecular weight 337;

6-Morpholino-3-(4-methylphenyl)-s-triazolo[4,3-b]pyridazine, melting at 207°–210° C.;

6-Morpholino-3-(3-ethozyphenyl)-s-triazolo[4,3-b]pyridazine, molecular weight 325;

6-Morpholino-3-(4-n-propylphenyl)-s-triazolo[4,3-b]pyridazine, molecular weight 323;

6-Morpholino-8-methyl-3-(4-bromophenyl-s-triazolo-[4,3-b]pyridazine, molecular weight 374;

6-Morpholino-8-ethyl-3(3-fluorophenyl)-s-triazolo[4,3-b]pyridazine, molecular weight 327;

6-Morpholino-8-methyl-3-(3-chlorophenyl)-s-triazolo[4,3-b]pyridazine, molecular weight 329.8, melting at 247°–248° C.; and 6-Morpholino-3-(4-methoxyphenyl)-s-triazolo[4,3-b]pyridazine, melting at 244°–247° C.

6-Morpholino-3-(4-fluorophenyl)-s-triazolo[4,3-b]pyridazine, melting at 214°–216° C.

6-Morpholino-3-(4-hydroxyphenyl)-s-triazolo[4,3-b]pyridazine, melting at 319°–322° C.

The compounds of the invention are useful as bronchodilators and can be formulated with conventional pharmacological carriers and administered to animals in a fashion similar to the customary procedures and formulations employed with known compounds known to have bronchodilator activity.

Bronchodilator activity of representative triazolopyridazine compounds of the invention is examined in the Konzett-Rossler guinea pig preparation according to accepted procedures. See Konzett and Rossler, Arch. f. Exp. Path. u. Pharmakol. 195: 71–74 (1940); Rosenthale and Dervinis, Arch. Int. Pharmacodyn. 172: 91–94 (1968). In this procedure an anesthetized guinea pig is artificially respired with a fixed volume of air. The volume of air is selected to slightly exceed the capacity of the guinea pig's lungs, and the excess air or overflow is measured. Test compounds are evaluated by administering a test compound intravenously 2 minutes prior to administration of an agonist compound (histamine, serotonin or acetylcholine) following 3 previous agonist doses resulting in relatively uniform (± 10 percent) bronchoconstriction. When the bronchospasm resulting from administration of the agonist compound occurs, the animal's lungs can receive less air, and hence the overflow is measurably increased. When a test compound blocks the bronchoconstriction induced by administration of the agonist compound, the results can be expressed quantitatively as a percent blockade. This is calculated by dividing the overflow agonist response measured after administration of the test compound by the average of the 3 preceding agonist responses, multiplying by 100 and subtracting this value from 100 percent. The results can also be expressed in comparison to a known bronchodilator, such as aminophylline. In such procedure, comparative results are expressed as "percent aminophylline", calculated by expressing the percentage blockade produced by a test compound as a percentage of the average percent blockade produced by dosages of aminophylline administered to the same test animal employed for the test compound with the aminophylline observations preceding and following the evaluation of the test compound in that animal.

In representative operations with triazolopyridazine compounds of the invention, administered intravenously at a dosage rate of 3 milligrams of test compound per kilogram of animal body weight (except as otherwise indicated) and using aminophylline at a dosage rate of 10 milligrams per kilogram and histamine as the agonist, the compounds and results in terms of percent blockade of histamine and percent of aminophylline are given in the following table. The compounds are identified by the 3-position substituent (R, R', R''-phenyl), and by $R_8$

| R, R', R''-Phenyl | $R_8$ | Percent Blockade | Percent of Aminophylline |
|---|---|---|---|
| Phenyl | H | 73 | 111 |
| 4-Chlorophenyl | H | 73 | 98 |
| 4-Methoxyphenyl | H | 47 | 78 |
| 3,4-Dichlorophenyl | H | 55 | 77 |
| 4-Tolyl | H | 66 | 81 |
| 3-Nitrophenyl | H | 50 | 66 |
| Phenyl | $CH_3$ | 46* | 92* |
| 4-Fluorophenyl | H | 70 | 110 |
| 2-Nitrophenyl | $CH_3$ | 21 | 29 |
| 3-Nitrophenyl | $CH_3$ | 56 | 76 |
| 4-Methoxyphenyl | $CH_3$ | 43 | 49 |
| 3-Methoxy-4-tolyl | H | 49 | 55 |
| 3,4,5-Trimethoxyphenyl | H | 43 | 64** |

*Administered at 10 mg/kg.
**Administered at 1.0 mg/kg.

In other operations using the compound 6-morpholino-3-phenyl-s-triazolo[4,3-b]pyridazine as the test compound at a dosage rate of 5 milligrams per kilogram, using the cat as a test animal, and using serotonin as the agonist, the test compound was found to give an 80 percent blockade of serotonin, equivalent to 199 percent of aminophylline activity. In such operations the test compound was administered by intravenous injection as a solution in a pharmacological carrier comprising 75 percent polyethylene glycol 200 and 25 percent sterile distilled water. The same test compound, when administered intravenously to guinea pigs at a dosage rate of 3 milligrams per kilogram as a aqueous solution of the hydrochloride salt was found to give a 65 percent blockade of acetylcholine, amounting to 131 percent of aminophylline activity.

In a comparison operation using histamine as the agonist compound, the compound of the invention 6-morpholino-3-phenyl-s-triazolo[4,3-b]pyridazine and comparison compound 6-piperidino-3-phenyl-s-triazolo[4,3-b]pyridazine of Pollak et al., supra were employed at a dosage rate of 3 milligrams per kilogram. In a series of operations, the 6-morpholino compound of the invention was found to give an average percent blockade of 72 ± 4, amounting to 111 percent of aminophylline. The comparision compound, having a piperidino substituent in the 6-position, produced a significantly lower response, an average of 32 ± 7 percent blockade, amounting to 38 percent of aminophylline. In addition, the 6-piperidino compound was observed to produce pronounced bronchoconstriction on injection to the guinea pigs, while the 6-morpholino compound did not produce such bronchoconstriction.

The starting materials used herein can be prepared by conventional procedures. For example, 380 grams of 3,6-dichloropyridazine, 950 grams of morpholine and 950 milliliters of absolute ethanol are mixed together and heated at the boiling temperature under reflux for 2 hours. The reaction mixture is cooled in an ice bath to 0° C. whereupon 3-chloro-6-morpholinopyridazine separates as a precipitate which can be collected by filtration. The 3-chloro-6-morpholinopyridazine can be converted to the corresponding 3-hydrazinopyridazine by reaction with excess hydrazine hydrate at the boiling temperature of the reaction mixture under reflux. In a representative procedure, 454 grams of 3-chloro-6-morpholinopyridazine and 4.75 liter of hydrazine hydrate are heated at the boiling temperature under reflux for 2 hours, after which the resulting solution is cooled to 0° C., whereupon a precipitate forms. The precipitate is collected by filtration, washed with 450 milliliters of hydrazine hydrate, dried and recrystallized from ethanol. Likewise, the benzoyl halides are readily available, and can be converted to the corresponding benzoyl hydrazides by reaction with hydrazine hydrate in a similar manner.

What is claimed is:
1. A 6-morpholino-3-substituted phenyl-s-triazolo[4,3-b]pyridazine compound corresponding to the formula

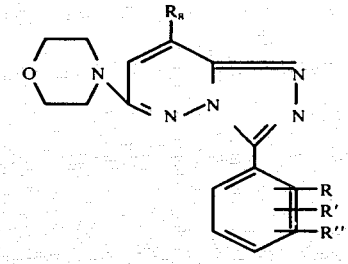

wherein R, R' and R'' each independently represent hydrogen, hydroxy, loweralkyl, lower alkoxy, halo or nitro, and wherein $R_8$ represents hydrogen or loweralkyl, and their pharmacologically acceptable salts.

2. A compound of claim 1 wherein $R_8$ is hydrogen.
3. A compound of claim 2 wherein R, R', R'' all represent hydrogen.
4. A compound of claim 1 wherein R, R', R'' are selected from hydrogen and methyl.
5. A compound of claim 1 wherein $R_8$ is hydrogen and wherein R, R', R'' are selected from hydrogen and methoxy.
6. A compound of claim 1 wherein R', R'', and $R_8$ represent hydrogen.
7. A compound of claim 1 wherein the compound is 6-morpholino-3-phenyl-s-triazolo[4,3-b]pyridazine.

* * * * *

UNITED STATES PATENT AND TRADEMARK OFFICE
CERTIFICATE OF CORRECTION

PATENT NO. : 4,016,162
DATED : April 5, 1977
INVENTOR(S) : Elivio Bellasio and Ambrogio Campi It is certified that error appears in the above-identified patent and that said Letters Patent are hereby corrected as shown below:

Title page, Item [54] first line, "6-MORPHOLINO-3-SUBSTITUTED" should read -- 6-MORPHOLINO-3-SUBSTITUTED- --.

Title page, Item [57] first line of ABSTRACT, "6-Morpholino-3--substituted phenyl triazolopyridazine" should read -- 6-Morpholino-3--substitutedphenyl triazolopyridazine --.

Column 1, first line of the title, "6-MORPHOLINO-3-SUBSTITUTED" should read -- 6-MORPHOLINO-3-SUBSTITUTED- --

Column 1, line 11, "J. Chem, Soc." should read -- J. Chem. Soc. --

Column 1, lines 35 to 40, this portion of the formula should read

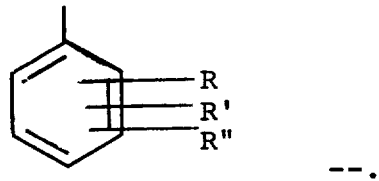

--.

Column 1, lines 54 and 55, delete the repetitious words "or the same loweralkyl, lower alkoxy, halo or nitro".

Column 1, line 63, "chloro" should read -- chloro or fluoro --.

Column 1, line 65, "chloro" should read -- chloro or fluoro --.

UNITED STATES PATENT AND TRADEMARK OFFICE
CERTIFICATE OF CORRECTION

PATENT NO. : 4,016,162
DATED : April 5, 1977
INVENTOR(S) : Elivio Bellasio and Ambrogio Campi It is certified that error appears in the above-identified patent and that said Letters Patent are hereby corrected as shown below:

Column 2, formula III, at line 35, should read

-- 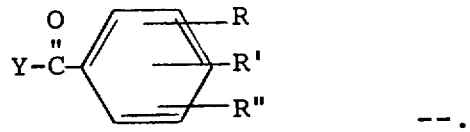 --.

Column 2, line 44, "X is hydrazine" should read --X is a hydrazine--.

Column 2, line 47, "at boiling" should read --at the boiling--.

Column 3, line 55, "8-methyl-6- -morpholino-3-phenyl-s-" should read --8-methyl-6-morpholino-3-phenyl-s- --.

Column 6, line 29, "6-Morpholino-8-methyl-3-(4-bromophenyl-s-" should read --6-Morpholino-8-methyl-3-(4-bromophenyl)-s- --.

Column 6, line 25, "6-Morpholino-3-(3-ethozyphenyl)-s-" etc. should read --6-Morpholino-3-(3-ethoxyphenyl)-s- --.

UNITED STATES PATENT AND TRADEMARK OFFICE
CERTIFICATE OF CORRECTION

PATENT NO. : 4,016,162
DATED : April 5, 1977
INVENTOR(S) : Elivio Bellasio and Ambrogio Campi It is certified that error appears in the above–identified patent and that said Letters Patent are hereby corrected as shown below:

Column 7, line 58, at the end of the line, "a aque-" should read --an aque- --.

Signed and Sealed this

Fifteenth Day of November 1977

[SEAL]

Attest:

RUTH C. MASON
Attesting Officer

LUTRELLE F. PARKER
Acting Commissioner of Patents and Trademarks